(12) United States Patent
Yates et al.

(10) Patent No.: US 10,743,764 B2
(45) Date of Patent: *Aug. 18, 2020

(54) WIDE FIELD FUNDUS CAMERA

(71) Applicant: Retivue, LLC, Charlottesville, VA (US)

(72) Inventors: Paul A. Yates, Charlottesville, VA (US);
Ming Lai, Pleasanton, CA (US)

(73) Assignee: Retivue, LLC, Charlottesville, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/267,713

(22) Filed: Feb. 5, 2019

(65) Prior Publication Data

US 2019/0167098 A1   Jun. 6, 2019

Related U.S. Application Data

(62) Division of application No. 15/510,923, filed as application No. PCT/US2015/049950 on Sep. 14, 2015, now Pat. No. 10,258,232.

(Continued)

(51) Int. Cl.
*A61B 3/125* (2006.01)
*A61B 3/00* (2006.01)
(Continued)

(52) U.S. Cl.
CPC ............ *A61B 3/125* (2013.01); *A61B 3/0008* (2013.01); *A61B 3/0025* (2013.01); *A61B 3/12* (2013.01); *A61B 3/14* (2013.01)

(58) Field of Classification Search
CPC ........... A61B 3/14; A61B 3/0025; A61B 3/12; A61B 3/102; A61B 3/0008

(Continued)

(56) References Cited

U.S. PATENT DOCUMENTS

| 3,944,342 A | 3/1976 | Martinez |
| 4,023,189 A | 5/1977 | Govignon |

(Continued)

OTHER PUBLICATIONS

International Search Report and Written Opinion, PCT/ISA/237, International Application No. PCT/US2015/049950, pp. 1-19, International Filing Date Sep. 14, 2015, Search Report dated Jan. 20, 2016.

*Primary Examiner* — Mohammed A Hasan
(74) *Attorney, Agent, or Firm* — Bond, Schoeneck & King, PLLC; Jeffrey Powers

(57) ABSTRACT

A wide field fundus camera is disclosed to implement multiple illumination beam projectors and to capture multiple retinal images at a various viewing angles to mimic wide field retinal examination with an indirect ophthalmoscope. The wide field fundus camera may incorporate a consumer image recording device with fast auto focusing so as to make the device quick to respond and easy to use. The wide field fundus camera may include narrow and broad slit beam illuminations to enhance autofocusing and imaging through less transparent crystalline lens and through haze due to Purkinje reflections from crystalline lens surfaces. Control of multiple illumination beam projectors in a programmable manner can be used to assess alignment of each illumination beam projector with the eye and to capture said multiple retinal images. Furthermore, a method is disclosed to montage said multiple retinal images into a single montage and to remove haze and reflections.

20 Claims, 10 Drawing Sheets

Related U.S. Application Data

(60) Provisional application No. 62/050,132, filed on Sep. 14, 2014.

(51) Int. Cl.
*A61B 3/12* (2006.01)
*A61B 3/14* (2006.01)

(58) Field of Classification Search
USPC .......................................................... 351/206
See application file for complete search history.

(56) References Cited

U.S. PATENT DOCUMENTS

| | | | |
|---|---|---|---|
| 5,822,036 A | 10/1998 | Maddie et al. | |
| 6,019,472 A | 2/2000 | Koester et al. | |
| 10,258,232 B2* | 4/2019 | Yates | A61B 3/0025 |
| 2008/0002152 A1 | 1/2008 | Collins et al. | |
| 2008/0259274 A1 | 10/2008 | Chinnock | |
| 2012/0229617 A1 | 9/2012 | Yates et al. | |
| 2012/0287255 A1 | 11/2012 | Ignotovich et al. | |
| 2013/0057828 A1 | 3/2013 | de Smet | |
| 2013/0335704 A1 | 12/2013 | Yates et al. | |
| 2014/0226128 A1* | 8/2014 | Lawson | A61B 3/0091 |
| | | | 351/206 |
| 2018/0228368 A1* | 8/2018 | Massie | A61B 3/102 |

* cited by examiner

WIDE FIELD FUNDUS CAMERA

CLAIM OF PRIORITY

This application is a divisional application of U.S. Non-Provisional application Ser. No. 15/510,923, filed Mar. 13, 2017, which claims benefit of priority under 35 U.S.C. 371(1) to International Patent Application Number PCT/US2015/049950, filed on Sep. 14, 2015, which claims priority to U.S. Provisional Patent Application No. 62/050,132, filed on Sep. 14, 2014, each of which are incorporated by reference herein in their entireties.

TECHNICAL FIELD

The present subject matter relates to a wide field fundus camera for photographing subject retinas.

BACKGROUND

Retinal images are broadly used for diagnosis of various diseases of the human retina. For instance, various retinal cameras have been routinely used to screen and to detect three of the most common eye diseases in adults: diabetic eye disease, glaucoma and age-related macular degeneration. Early detection of these diseases can delay and prevent subsequent loss of vision. The conventional retina cameras used to perform these screening exams typically have a central 45 to 60 degree field of view (FOV) representing less than 10% of the entire surface area of the retina, but focused on the optic nerve and macula most affected by these diseases and responsible for loss of central vision.

In contrast, wide field retinal images, referring to a greater than 60 degree FOV, are commonly used in the diagnosis of retinopathy of prematurity (ROP), a retinal disease of premature infants. At advanced stages ROP can result in retinal detachment with permanent vision loss, but is often treatable with early routine screening and detection. Traditionally, ROP is typically diagnosed via manual physician exam using an indirect ophthalmoscope. The examining physician utilizes indirect ophthalmoscopy, and relies on scleral depression to visualize the retinal periphery to the ora serrata over 8 cardinal positions (12, 1:30, 3:00, 4:30, 6:00, 7:30, 9:00, and 10:30). Given that pathology associated with ROP occurs predominantly in the retinal periphery, a minimum 120 degree FOV of the retina is required for proper diagnosis. Traditional screening and diagnosis of ROP requires a highly skilled ophthalmologist to perform this exam and correctly document their retinal findings. It is a time consuming process and it lacks reliable documentation, with most ophthalmologists still performing sketched drawings to represent their retinal findings.

Wide field retinal images in a digital format can be obtained with the Retcam from Clarity Medical Systems (Pleasanton, Calif., United States of America). In one approach, a wide field fundus camera employs an illumination ring as shown in U.S. Pat. No. 5,822,036 (Massie et al.) located at the tip of a hand piece housing the illumination light source, imaging optics and camera sensor. The illumination ring is formed with a bundle of optical fibers and projects bright illumination through the entire pupil. The device provides uniform illumination over a field of view to produce a retinal image with a 120 degree FOV of the retina. Use of such a configuration may lack clarity in the image when the crystalline lens is less transparent and when the Purkinje reflection images from the crystalline lens surfaces become visible inside the field of view. Use of such a configuration may be suitable newborn babies and infants with a highly transparent crystalline lens, but may be less suitable for patients with a less transparent lens, in particular adults.

SUMMARY

Newborn babies and infants may have a less-transparent crystalline lens, due to various clinical conditions. Image haze may appear due to lens scattering inside a less-transparent crystalline lens wherever the illumination beam path overlaps with imaging beam path. This image haze may stem from Purkinje reflection images from crystalline lens surfaces. Image haze may be improved by separating the illumination beam path from the image beam path inside the crystalline lens. This configuration can be found in conventional retinal cameras, but with a limit on field of view of 45 to 60 degrees and with various masks on the illumination beam path to create an image window throughout the crystalline lens. However, such a configuration remains a challenge to implement for a wider field of view fundus camera.

Another highly desirable feature for fundus cameras would be a quick and reliable auto focus. Unlike conventional tabletop fundus cameras, a wide field fundus camera for ROP screening is typically a handheld device and thus fast response of the camera may improve the usability of the device. Generally, auto focus found in conventional tabletop fundus cameras is much slower than found in consumer image recording devices. There have been prior attempts to implement a consumer image recording device with fast auto focus into a handheld fundus camera.

In US patent application publication US 2012/0229617, titled "Hand-Held Portable Fundus Camera for Screening Photography," Yates et al. disclose how to implement a consumer image recording device into a handheld fundus camera to utilize auto focus mechanisms built into a consumer camera. Another concern is the reliability as auto focus in consumer image recording devices may rely on well-illuminated and high contrast features to perform, while retinal images may lack such well-illuminated and high contrast features. In US patent application publication US 2013/0335704, titled "Intuitive Techniques and Apparatus for Ophthalmic Imaging," Yates et al. disclose how to project a diffractively-modified laser beam to create well-illuminated and high contrast features on the retina to enhance auto focusing. A further challenge arises as to how to implement the concept with non-coherent light and how to improve performance through less-transparent crystalline lenses.

The present inventors have recognized, among other things, that auto focusing and imaging through a less-transparent crystalline lens remain challenging issues for wide field fundus cameras with a wide field of view. Meanwhile, instrumenting an indirect ophthalmoscope into a digital format and adapting a consumer image recording device and its fast auto focus have yet to be implemented for wide field fundus cameras.

An example according to the present subject matter may include a wide field fundus camera incorporating multiple illumination beam projectors, of which each illumination beam projector mimics the illumination conditions of an indirect ophthalmoscope. An example according to the present subject matter thus may include to take multiple retinal images at various viewing angles to mimic viewing conditions of the indirect ophthalmoscope. An example according to the present subject matter also may include implementation of a wide field fundus camera with a consumer image recording device that enables autofocus, auto exposure, real-time display and wireless transfer of high definition images. An example according to the present subject matter further may include to project a narrow slit beam at an angle to enhance auto focus through a less-transparent crystalline lens. An example according to the present subject matter also further may include implementation of a broad slit beam into each of multiple illumination beam projectors to better image through a less-transparent crystalline lens. An example according to the present subject matter even further may include implementation of image processing to stitch multiple retinal images into an evenly exposed single field image.

More specifically, an example according to the present subject matter discloses a wide field fundus camera, comprising:
- an aspherical lens having a symmetric viewing axis and disposed to form a retinal image;
- an image recording device configured to provide one or more of auto focus and auto exposure and aligned with said aspherical lens to capture said retinal image;
- a first source configured to provide of a plurality of illumination beam projectors positioned around said viewing axis and projected each at an angle toward said aspherical lens;
- a second source configured to provide a narrow illumination beam projector projected at an angle and away from pupil center to provide a bright feature on retina to enhance auto focusing through less-transparent crystalline lens;
- cross polarization optics incorporated between said first and second sources of illumination beams and said image recording device to reject specular reflections of said illumination beams;
- an electronic control circuit configured to provide a system to control said plurality of illumination beam projectors and facilitating capture of a plurality of retinal images in a programmable manner, and configured to process said captured plurality of retinal images to stitch the captured plurality of images into a wide-field composite image.

Therefore, a first aspect of the present subject matter can include providing a wide field fundus camera implementing multiple illumination beam projectors and multiple retinal images at various viewing angles to mimic retinal examination with an indirect ophthalmoscope. A second aspect of the present subject matter can include use of a consumer image recording device having fast auto focusing so as to make a wide field fundus imaging apparatus quick to respond and easy to use. A third aspect of the present subject matter can include providing narrow and broad slit beam illuminations to enhance autofocusing and imaging through less transparent crystalline lens and reflection haze. These and other aspects of the invention will become more apparent in the following drawings, detailed description, and claims.

DETAILED DESCRIPTION

Figure 1:
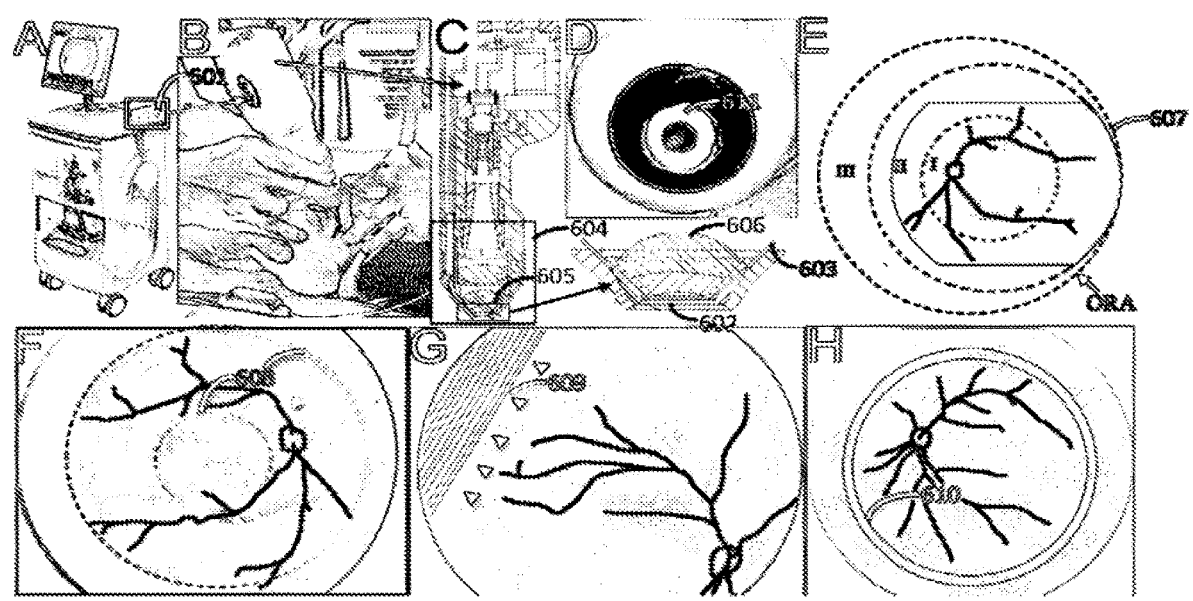
FIG. 1. illustrates a generally-available camera and related techniques for ROP screening.

FIG. 1 shows the Retcam contained on a rolling cart with a handheld imaging camera 601. A computer on the cart connects to the camera sensor inside the handheld imaging camera. Halogen illumination on the cart connects via fiber optic cable to the handpiece. B The contact lens 602 of the handpiece is positioned on the neonate's cornea following dilation and lid speculum placement C, D Fiber optic illumination 603 is routed thru the lens module 604 to the front of the handpiece 605 at the sides of the imaging lens 606 to create ring illumination 611. E Representative field of the entire retina divided into zones I, II, and III used for retinopathy of prematurity screening (ROP). Direct ring illumination may cover a 120 degree field of view allowing macular centered pictures to reach zone II of the retina, but requiring repositioning of the handpiece in up to 9 locations to fully image the entire peripheral retina in zone III to the Ora Serrata 607. F Ring illumination may create a "donut" in some patients 608, with illumination falling off peripherally and centrally. G Some peripheral details of retina such as a demarcation line associated with ROP (609—white arrows) may be less visible if there is insufficient peripheral illumination of the retina. H In adult patients there may be prominence of the human lens reflection (Purkinje III and IV reflection) of the ring illumination, which occurs due to changes in refractive power of the human lens following the neonatal period 610.

Figure 2:
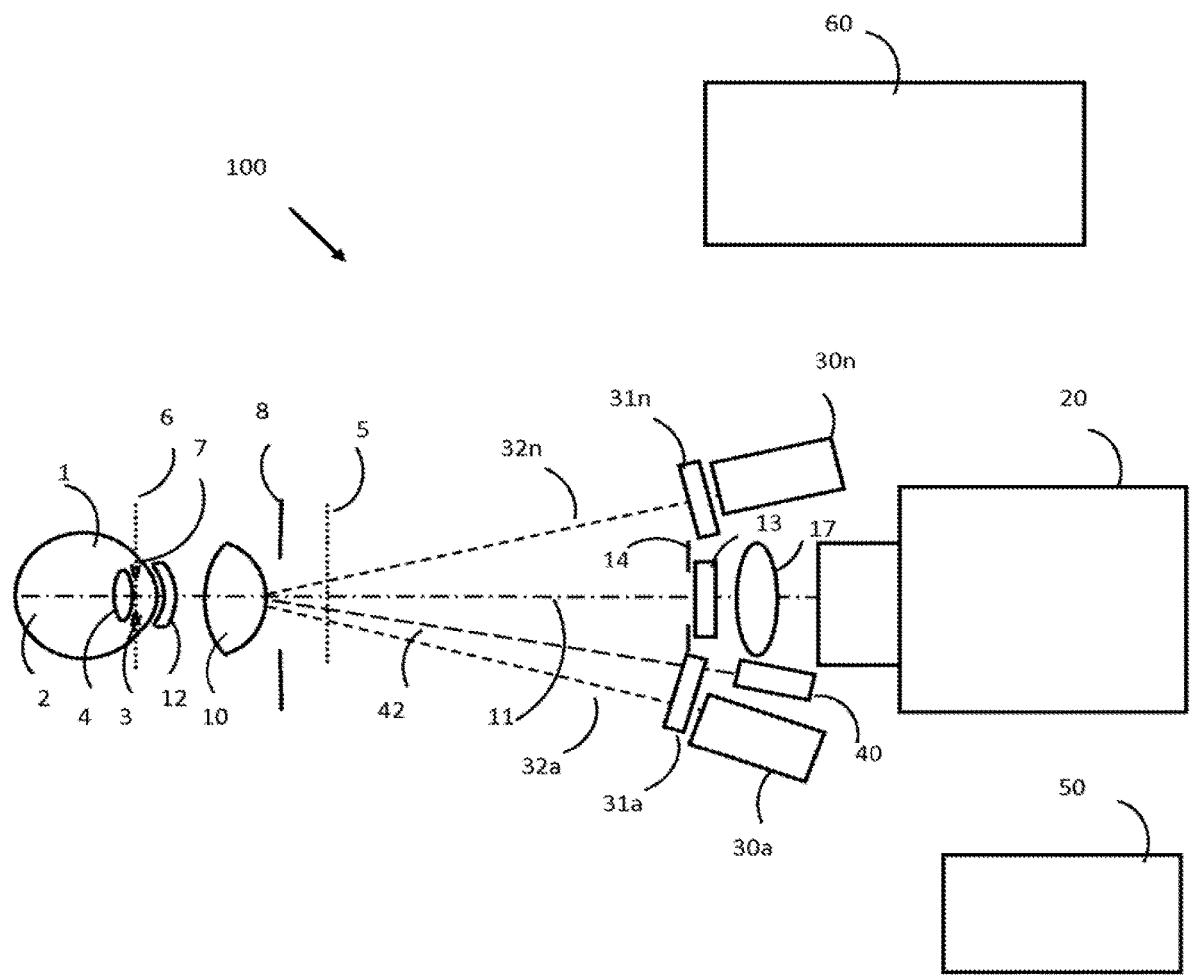
FIG. 2 shows an illustrative example of a wide field fundus camera implemented using multiple illumination beam projectors and a narrow beam projector.

FIG. 2 shows an illustrative example of a wide field fundus camera 100 with multiple illumination beam projectors 30a-30n and a narrow beam projector 40. The wide field fundus camera 100 includes primarily an objective lens 10, an image recording device 20, a plurality of illumination beam projectors 30a-30n, a narrow beam projector 40, a first polarizer 13 and a set of second polarizers 31a-31n. The wide field fundus camera 100 further includes a contact lens 12, a focusing lens 17, an electronic controller 50 and an image display 60.

Objective lens 10 may be an aspherical lens and is located at a first end of the wide field fundus camera 100. The objective lens 10 defines a symmetric viewing axis 11 and a working plane 6 of the wide field fundus camera 100. The plurality of illumination beams 32a-32n emerging through an illumination aperture 8 are pre-focused at the working plane 6. When a subject eye 1 is aligned with the wide field fundus camera 100 for fundus viewing, subject pupil 3 is about to position at the working plane 6 and the illumination beams 32a-32n are projected into subject pupil 3 to illuminate the subject retina 2 for alignment and for photographing. At a proper alignment, objective lens 10 produces a first retina image near its back focal plane 5, and the first retina image is then re-imaged into the image recording device 20. The illumination aperture 8 is located at the back focal plane 5 so as to define illumination area on the subject retina 2.

At a proper alignment, objective lens 10 also forms an image of the subject pupil 3 onto the plane of optical stop 14, which thus defines a small, virtual viewing window on the subject pupil 3 for the camera 20 to look through into the retina 2. The illumination beams 32a-32n are thus respectively focused at the subject pupil 3 and the focal spots are pre-positioned outside the virtual viewing window. Therefore, any scattering light of illumination beams 32a-32n scattered outside this virtual viewing window will be substantially blocked from getting into the image recording device 20.

In an illustrative example, the wide field fundus camera 100 may provide a static field of view of 120 degrees or wider on the subject retina 2. In this illustrative example, the objective lens 10 has an optical power of about 120 D and a diameter of about 18 mm. The objective lens 10 has thus a back focal length of shorter than 8 mm and a small working distance of approximate 4 millimeters with respect to the subject cornea 7. The objective lens 10 may be an aspherical lens such that to have relative lightweight and to produce optimal image quality over the subject retina 2.

A contact lens 12 may be positioned in front of the aspherical objective lens 10 and in direct contact with the subject cornea 7. The contact lens 12 may or may not have optical power. FIG. 2 shows how a contact lens 12 is incorporated with the aspherical objective lens 10 to produce a first retinal image of the retina 2. In an illustrative example, the contact lens has a diameter of about 10 mm to fit for the small eyeball 1 of infants.

There are commercially available aspherical lenses for retinal viewing, with indirect ophthalmoscopes or slit lamp microscopes. For instance, an aspherical lens integrated with a contact lens can be found in an Ocular ORMR-2x (Ocular Instruments, Bellevue, Wash., United States of America).

The image recording device 20 is located at a second end of the wide field fundus camera 100 and is to view and to photograph fundus image through objective lens 10. Also, this image recording device 20 is in an illustrative example able to perform auto-focusing and auto-exposure control. The image recording device 20 in an illustrative example may include a consumer image recording device that includes advanced features of auto-focus, auto-exposure, real time display, and image storage and transfer, and that is compact, lightweight, and easy to use. The image recording device 20 may have built-in function to readily transfer its recorded image to a local computer or other processor for internet connectivity and telemedicine networks. The image recording device 20 as an illustrative example may have a resolution over 2 mega pixels and have an entrance pupil of 8 mm or bigger to receive all light passing through the optical stop 14. The image recording device 20 may have a feature of a custom setting and be capable of saving working parameters for convenient operation. The image recording device 20 may have a separate display 60 for easy viewing, to provide a desirable viewing angle, display size, and display distance.

The image recording device 20 in an illustrative example is a smart lens type of consumer camera, such as a Sony QX100 (Sony Corporation, Japan). In this illustrative example, the image recording device 20 is coupled with the display 60 via Wi-Fi, and the display 60 may be a wireless device such as an iPhone or an iPad. Also this image recording device 20 may have high sensitivity and high resolution operation.

The plurality of illumination beam projectors 30a-30n may include two or more illumination beam projectors 30a-30n. Each of the projectors 30a-30n projects an illumination beam 32a-32n at an angle toward the objective lens 10. In an illustrative example, each illumination beam 32a-32n has a small vergency and has a beam size to cover the illumination aperture 8. This way, each illumination beam 32a-32n is to mimic the illumination of an indirect ophthalmoscope and to illuminate a portion of an image on the subject retina 2. In an illustrative example, the plurality of illumination beam projectors 30a-30n produces four illumination beams 32a-32n, of which each illuminates a quadrant of the field of view on the subject retina 2.

A wide field fundus camera 100 may be operated in the mydriatic condition, and white light illumination can be used for both aligning and photographing the subject retina 2. In an illustrative example, each of the plurality of illumination beam projectors 30a-30n includes a high brightness, high power white LED and a projection lens to produce a white light illumination beam 32a-32n. The white light LED may include a warm white light source with a color temperature about 3000 degrees of Kelvin. For radiation safety, each illumination beam 32a-32n is limited to project a few milli-watts of illumination power.

When another illumination condition is desirable, the illumination beam projectors 30a-30n can include one or more of high power, high brightness infrared LEDs. Further, the illumination beam projectors 30a-30n can include one or more of high power, high brightness LEDs capable of projecting a limited spectral range of illumination such as red, green, or blue light.

The projection angle of the illumination beams 32a-32n may be set so as to move corneal and crystalline lens reflections away from central viewing area. On the other hand, the projection angle of the illumination beams 32a-

32n is limited to the minimum pupil size that the wide field fundus camera 100 is intended to use. For screening for ROP, the minimum pupil size is set to approximately 5 mm, and the projection angle of the illumination beams 32a-32n is thus set to about 10 to 15 degrees.

The narrow beam projector 40 is to project a narrow illumination beam 42 and to form a bright illumination feature on the retina 2 to facilitate auto focusing of the image recording device 20. Typically, a consumer image recording device 20 requires a relatively high illumination level and a relatively high contrast target feature to obtain reliable and effective auto focusing. A bright and narrow slit beam illumination on or near the center of retina 2 is illustrated. In one illustrated example, the dimensions of the slit beam are about 3 mm long and 1 mm wide on the retina 2.

The narrow illumination beam 42 is to project at an angle with respect to the viewing axis 11. In an illustrative example, the narrow slit beam 42 is focused outside the virtual image window and has no overlap with the image beam path throughout the crystalline lens 4.

The first polarizer 13 and the set of second polarizers 31a-31n may form a cross polarization condition to reject specular reflections of the illuminations beams 32a-32n back into the image recording device 20. For a predetermined orientation of the first polarizer 13, each of the second polarizers 31a-31n may be rotationally adjusted to form a precise condition of cross polarization. Specular reflections at surfaces of the objective lens 10 and contact lens 12 are particularly strong and necessary to remove. Specular reflections from first corneal surface (i.e. first Purkinje reflection), first surface of crystalline lens (i.e., third Purkinje reflection) and second surface of crystalline lens (i.e., fourth Purkinje reflection) can be a major source of image haze. A high extinction ratio of cross polarization is required for reflection haze reduction. The polarizers 31a-31n and 13 may be selectively thin film polarizers and have an extinction ratio of 300 or higher throughout the visible and infrared light spectrum.

The contact lens 12 may serve as an optical window of the wide field fundus camera 100 to interface with the subject cornea 7. The contact lens 12 is illustrated to have an anti-reflection coating on its convex surface. As the illumination beams 32a-32n and the narrow illumination beam 42 are small and bright on the contact lens 12, effort is required to minimize and to remove specular reflection from its convex surface that interfaces to air.

The focusing lens 17 in one illustrative example is an achromatic lens with a focal length about 60 mm to 80 mm and is positioned one focal length away from the back focal plane 5 of the objective lens 10. In one illustrative example, the collimation lens 17 is to reimage the first retinal image formed by the objective lens 10 into distance, and thus the image recording device 20 is operated to focus at distance. This way, the focal length of camera 20 can be adjusted continuously to match a desirable field of view and the selected retinal image area can thus fill up the camera display 60. As a result, the pixel resolution of the camera and its display can be optimized. Focusing lens 17 and objective lens 10 may form an optical afocal relay, to relay the outgoing beam from the subject pupil 3 to the image recording device 20. The optical afocal relay has a scaling factor m, equal to the ratio of the focal lengths between the focusing lens 17 and the objective lens 10. In an illustrative example, the focusing lens 17 has a focal length of 60 mm, and the optical afocal relay has a scaling factor m of about 7.5.

Optical stop 14 may be positioned in front of the image recording device 20 and is conjugated with the working plane 6 of the wide field fundus camera 100 via objective lens 10. The optical stop 14 has an aperture corresponding to a predetermined virtual viewing window on the subject pupil 3. For instance, for a scaling factor of 7.5 and a virtual viewing window of 1.3 mm on the subject pupil 3, the optical stop 14 is thus 10 mm. In operation, the subject pupil 3 is aligned with the working plane 6, and the optical stop 14 blocks any light scattered from outside the virtual viewing window on the subject pupil 3. The aperture of the optical stop 14 may also be limited to the effective aperture of the image recording device 20.

The electronic controller 50 is to couple with the image recording device 20 and to power the illumination projectors 30a-30n and the narrow beam projector 40. In an illustrative example, the electronic controller 50 powers the illumination projectors 30a-30n at a low power level during alignment and then ramps up them to a high power level for photographing the subject retina 2. The power level of each of the illumination projectors 30a-30n can be controlled in a programmable manner. This way, the illumination projectors 30a-30n can be synchronized with the image recording device 20 to take multiple retinal images with various on-off configurations and time sequences.

The display 60 may couple with and display real-time images of the image recording device 20. In an illustrative example, the display 60 is a high definition monitor and is coupled wirelessly with the image recording device 20. For instance, the image recording device 20 may be a Sony QX100 (Sony Corporation, Japan) and the display may be an iPad (Apple, Cupertino, Calif., United States of America) and data transfer between the two devices may be through Wi-Fi built into the devices.

The images captured by the image recording device 20 may be stored in the camera 20, monitored at the display 60, and transferred to a local computer or other networked computers. The images captured by the image recording device 20 may thus be viewed through the network, and retinal diseases can be diagnosed by a retinal professional in a local or remote location.

A digital controller 50 may be used to independently control each illumination beam projector 30a-30n. In an illustrative example there are four independent LED beam projectors controlled by a digital controller. The controller may be connected to a tablet through its USB port and the user interface to the image recording device 20 and the digital controller 50 may be provided on the tablet display.

Figure 8:
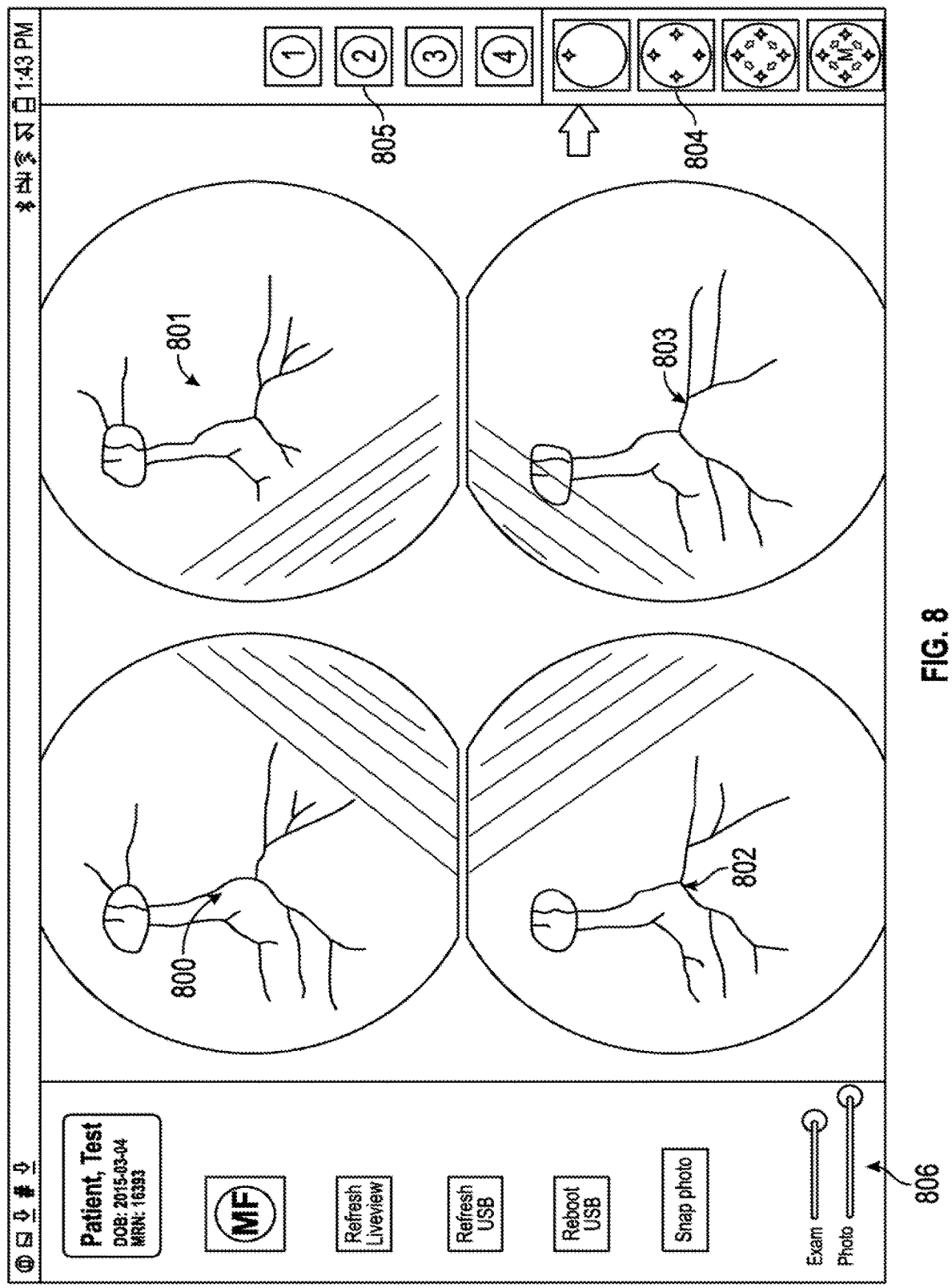
FIG. 8 shows an illustrative example of the tablet display demonstrating real-time live view display of the retinal image formed by four independent projector beams that may allow proper user alignment with the eye. Additionally user controls to set real-time illumination level, photo flash illumination level, pattern of independent projector beam illumination control, and independent manual control of each projector beam are shown.

In FIG. 8, an illustrative examples demonstrates how the user can control each of the four independent beam projectors 30a-30n and turn each one on or off via an illumination pattern selector 804. The independent beam projectors 30a-30n may also be serially programmable and the pattern, timing, and beam illumination intensity can be controlled by the user via an illumination mode selector 805. Power level for each independent beam projector 30a-30n may be controlled for both real-time live-view imaging of the retina, as well as flash photography via an illumination level adjustor 806, wherein for flash photography the illumination beam projectors 30a-30n may be temporarily adjusted to higher intensity than in live-view imaging mode, for the purpose of final photo acquisition or auto-focusing purposes. Rapid sequential serial illumination control of each independent beam projector 30a-30n may allow the retinal view provided by each independent beam projector to be shown simultaneously in separate live-view images of the retina 800, 801, 802, 803 For example one of four independent illumination beam projectors 30a-30n can be individually turned on and the retinal image resulting from each of four independent beams then shown in four separate panels on the same display 800, 801, 802, 803. In an illustrative example, each independent beam projector 30a-30n may be turned on for less than 100 ms, serially turning on each beam projector 30a-30n one at a time, allowing acquisition of the views provided by each of the four independent beam projectors in less than 400 ms. This timing can prevent lag in the live-view and allow the user to align the camera with the eye to optimize illumination provided by each independent beam projector 30a-30n.

Figure 10:
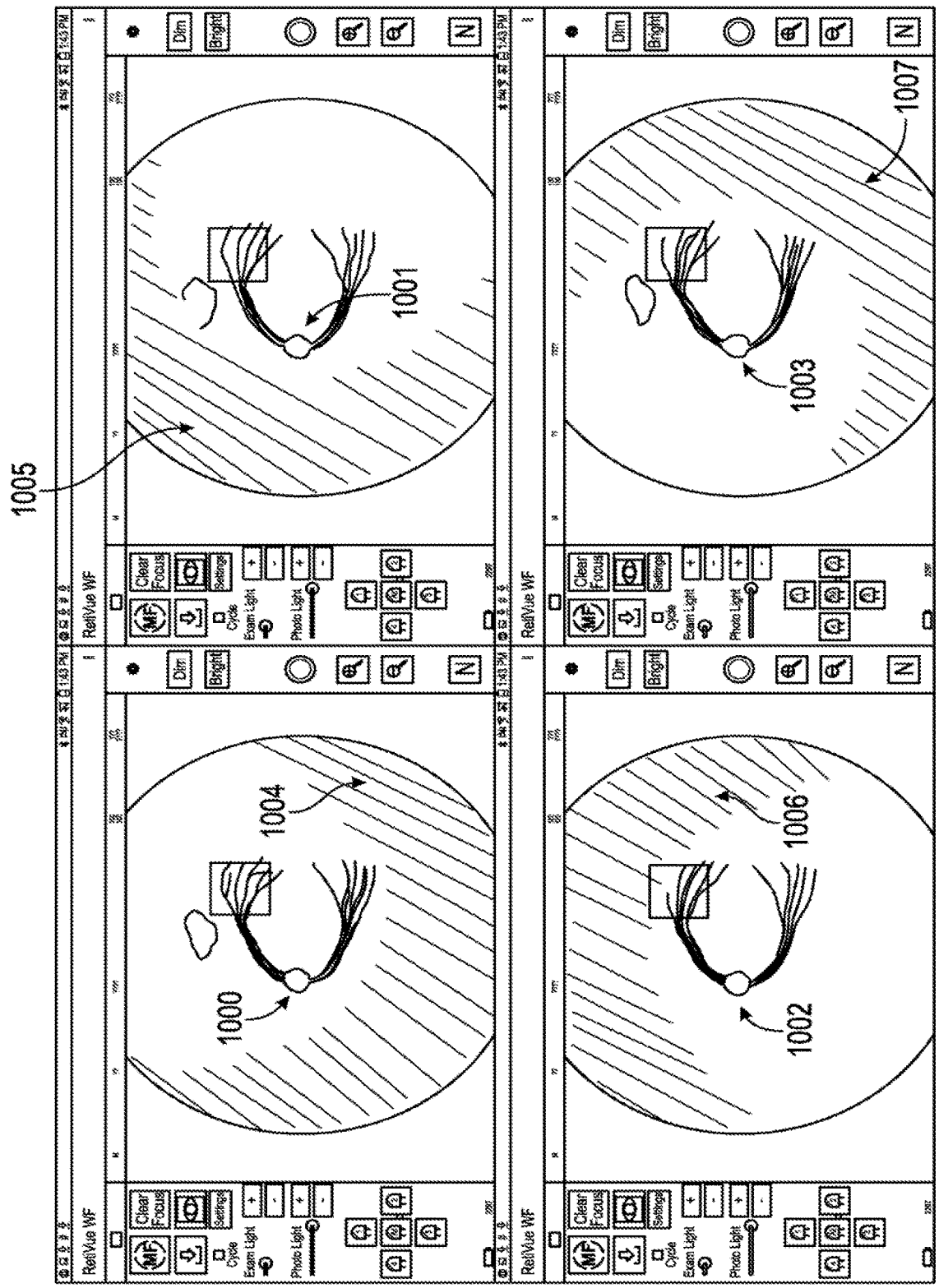
FIG. 10 shows an illustrative example of the live-view display formed by the electronic controller and image recording device at four different points in time. At each point in time, a single independent projector beam may be illuminated, with each of four separate independent projector beams illuminated in a serial manner as shown in the four panels. The display would appear to the user real-time as a rotating illumination beam that may allow the user to assess alignment of each illumination projector beam with the eye before final image acquisition.

In a separate illustrated example in FIG. 10, a single live view image of the retina may be provided, and each independent beam projector 30a-30n can be turned on and then off for a discrete period of time in a rotating clockwise or other programmed manner, one or more projector beams at a time, to allow the user to see the illumination provided by each beam projector for assessing alignment of the camera with the eye prior to final retinal image acquisition. For example, one of four independent beam projectors 30a-30n may be turned on for 250 ms 1000, then turned off, then the next independent beam projector is turned 1001 on for 250 ms, then turned off, then the next independent beam projector is turned 1002 is turned on for 250 ms, then turned off, then the next independent beam projector is turned 1003 is turned on for 250 ms. This sequence of beam illumination control could be repeated until a final retinal image is acquired. The four panels shown in FIG. 10 1000, 1001, 1002, 1003 provide an example display seen at four different points in time, and would appear to the user as a rotating beam in real-time. Each independent beam projector 30a-30n may create a clear quadrant of viewing of the retina 1000, 1001, 1002, 1003 as well as an area of lens haze and reflections 1004, 1005, 1006, 1007 due to scattering of the illumination beam in objective lens 10, and the human lens 4.

A method may be used to process the multiple retinal images provided by each independent projector beam 30a-30n and to stitch them into a single fundus image. An illustrative example of this method is a processor circuit coupled to a memory circuit, the memory circuit including instructions that cause the processor circuit to receive imaging information corresponding to the plurality of retinal images and to provide a composite image including stitching together the plurality of retinal images into a single montage image. Please refer to FIG. 9. In an illustrative example, a plurality of retinal images are acquired for four independent beam projector 30a-30n, turned on sequentially one at a time with the separate acquired retinal images shows as 900, 901, 902, and 903. Image haze from the specular reflections from the human lens is evident in each image and is indicated by 906, 907, 908, and 909. The portion of the each image without human lens haze 900, 901, 902, 903 using said method can be stitched together to form a final montage image 905. Blending may be performed of the separate images that form the final montage to eliminate seams and even exposure across the final montage. The method used to process said multiple retinal images may also identify the human lens haze (906, 907, 908, 909), for illustrative example by both its contrast level and characteristic position based on which independent illumination projection beam is on and the angle the projection beam has with the eye. This haze may be masked by said image processing method before performing the final montage.

Figure 3:
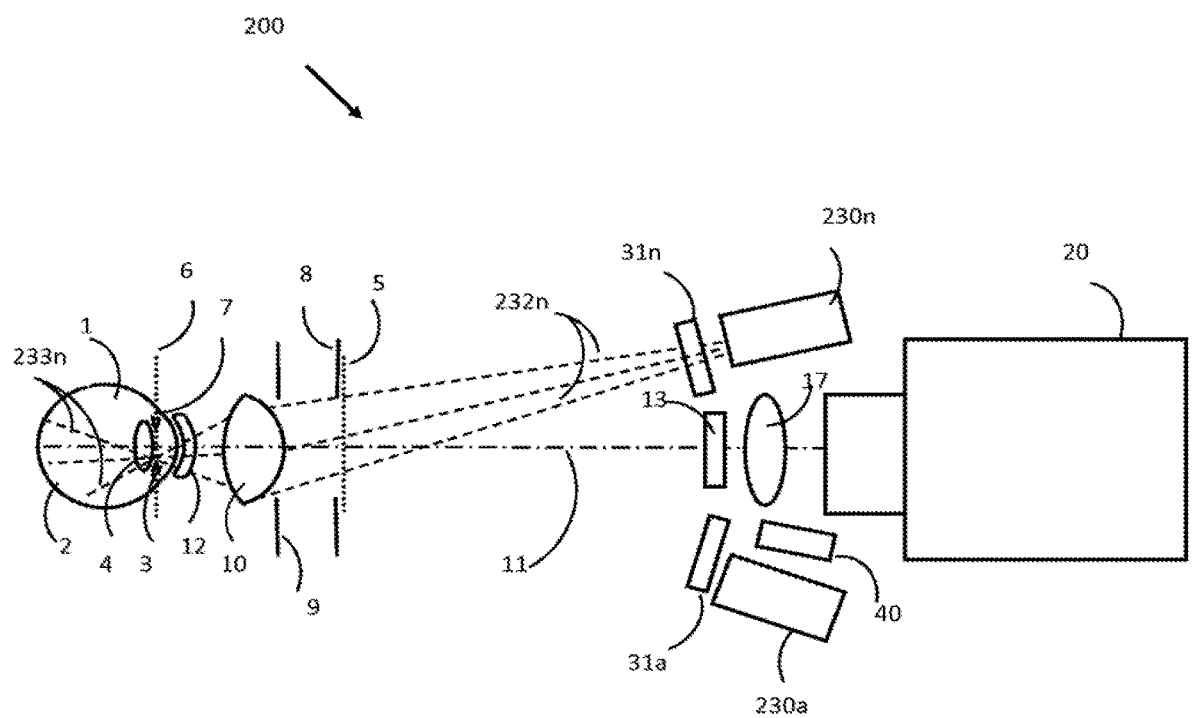
FIG. 3 shows an illustrative example of a wide field fundus camera having one of the multiple illumination beam projectors turned on for taking one of the multiple retinal images.

FIG. 3 shows an illustrative example of a wide field fundus camera 200 having an illumination beam projector 230n turned on for taking one of the multiple retinal images. The illumination beam projector 230n projects an illumination beam 232n onto the objective lens 10 at an angle with respect to the viewing axis 11, mimicking the illumination configuration of an indirect ophthalmoscope. The illumination beam 232n is then focused on the working plane 6 and directed into subject pupil 3. This illumination beam 232n passes through the subject pupil 3 and turns into illumination beam 233n to illuminate subject retina 2.

Because the illumination beam 232n is projected at an angle and is shaped by the apertures 8 and 9, the illumination beam 232n can thus be focused into subject pupil 3 and be away from the pupil center. In an illustrated condition, the illumination beam path is not overlapped with the image beam path inside the crystalline lens 4, and scattering light scattered from the crystalline lens 4 is not captured by the image recording device 20. In this way, image haze resulting from lens scattering of the illumination beam inside a less-transparent crystalline lens may be significantly reduced.

Also because the illumination beam 232n is projected at an angle and is shaped by the apertures 8 and 9, the illumination beam 233n is not symmetric on the subject retina 2. More than a quadrant of the field of view may be illuminated via such an illumination configuration. At this illumination condition, an image captured by the image recording device 20 may show only a portion but not the full field of view being illuminated. Therefore, multiple images may be required to capture the subject retina 2 in order to have a full field of view. In an illustrative example, four illumination beam projectors 230 are used and four retinal images may be captured in time sequence to provide a 120 degree field of view of the subject retina 2.

Figure 4:
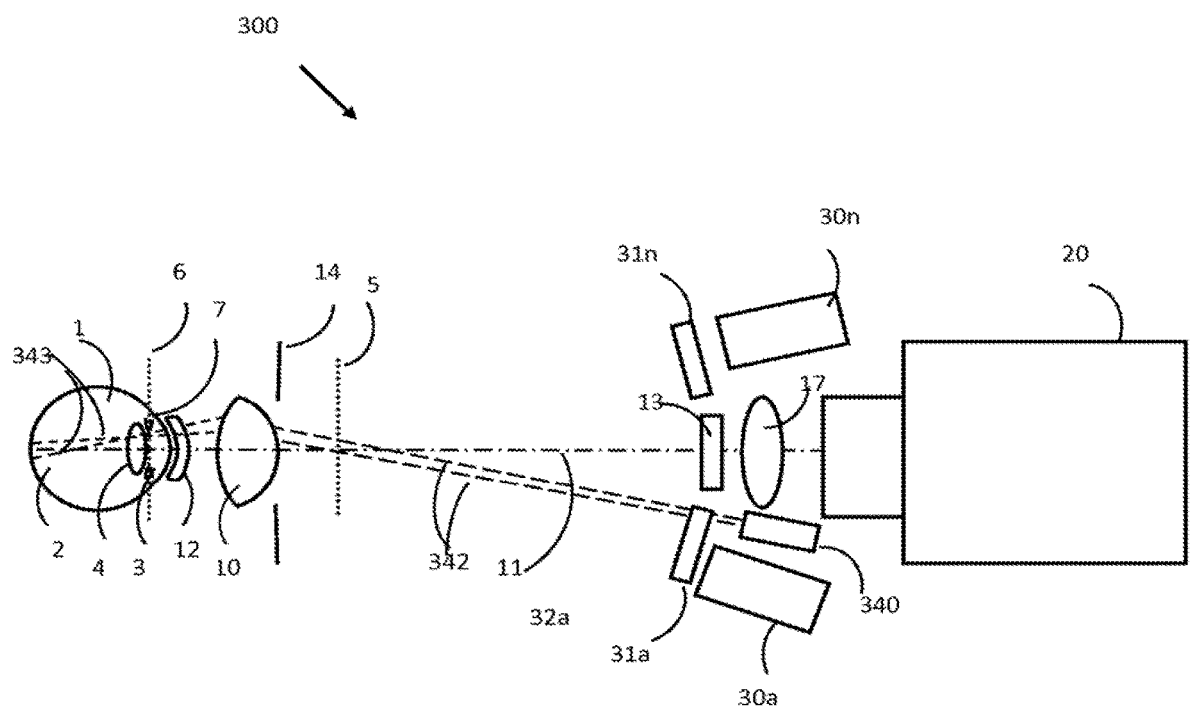
FIG. 4 shows an illustrative example of a wide field fundus camera having the narrow beam projector turned on to facilitate autofocusing through less transparent crystalline lens and reflection haze.

FIG. 4 shows an illustrative example of a wide field fundus camera 300 having the narrow beam projector 340 turned on to facilitate autofocusing through less transparent crystalline lens 4 and reflection haze. The narrow beam projector 340 is to project a narrow illumination beam 342 and to form a bright illumination feature on the subject retina 2. A consumer image recording device 20 may require a relatively high illumination level and a relatively high contrast target feature to obtain reliable and effective auto focusing. In particular, a bright and narrow slit beam illumination on or near the center of the subject retina 2 may be favorable for such autofocusing. In one illustrated example, the dimensions of the slit beam are about 3 mm long and 1 mm wide on the subject retina 2.

The narrow slit beam 342 can be projected at an angle with respect to the viewing axis 11. In an illustrative example, the narrow slit bean 342 is focused outside the virtual image window and has no overlap with the image beam path throughout the crystalline lens 4. This way the slit beam image on the image recording device 20 is not blurred by scattering light from the crystalline lens 4, and the narrow slit beam 342 thus serves to facilitate autofocusing through less transparent crystalline lens 4.

Figure 5:
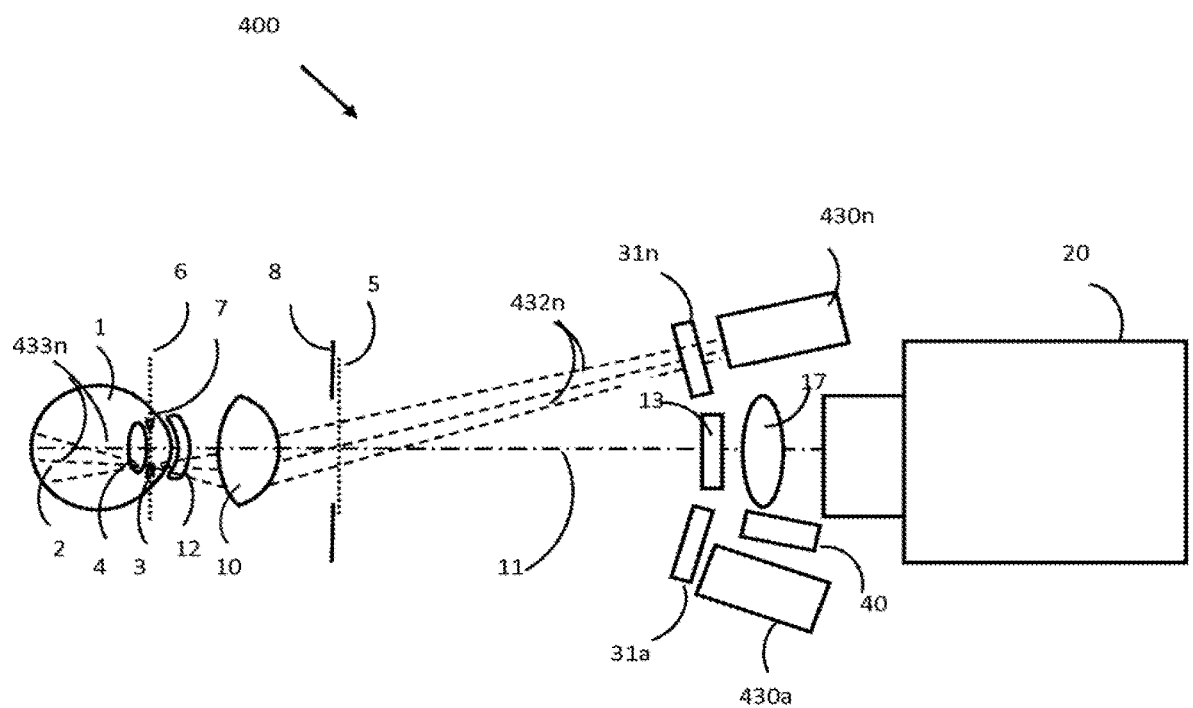
FIG. 5 shows an illustrative example of a wide field fundus camera having one of the multiple slit beam projectors turned on to improve image taking through less transparent crystalline lens and reflection haze.

FIG. 5 shows one illustrative example of a wide field fundus camera 400 having one slit beam projector 430n turned on to improve image taking through less transparent crystalline lens 4 and reflection haze. The slit beam projector 430n projects a slit beam 432n toward the objective lens 10, in which the slit beam 432n has a narrow dimension in the incident plane of the illumination and a full dimension normal to the incident plane. As shown in FIG. 5, such a slit beam 432n turns into a slit illumination beam 433n on the subject retina 2. Also, such a slit beam 432n is confined away from the viewing axis 11 and thus may have a better clearance with the image beam path inside the crystalline lens 4. Consequently, an overlapping region between the illumination beam path and the image beam path can be avoided inside the crystalline lens 4, and thus image haze due to light scattering inside less transparent crystalline lens 4 may be substantially improved.

In an illustrative example, the slit beam 432*n* of FIG. 5 may provide a retinal slit image of approximate 60 degrees in the narrow dimension and 120 degrees in the length dimension, i.e., a dimension normal to the incident plane of the page. In one illustrative example if such a retinal slit image is taken at a rotational angle of 60 degrees separate from each other, then three of such retinal slit images may cover the full image of the subject retina 2. In an illustrative example, three slit beam projectors 430*a*-430*n* are positioned 120 degrees from each other around the symmetric viewing axis 11, and each projects a slit beam 432*n* with its narrow dimension orientated in its own incident plane. In this case, three retinal images may be taken to form a complete full field of view of the subject retina 2. Similarly, in another illustrative example if the slit beam narrow dimension is about 40 degrees, five of slit beam projectors 430*a*-430*n* may be used and five slit beam images taken to cover a full field of view of the subject retina 2 with the objective lens 10.

Figure 6:
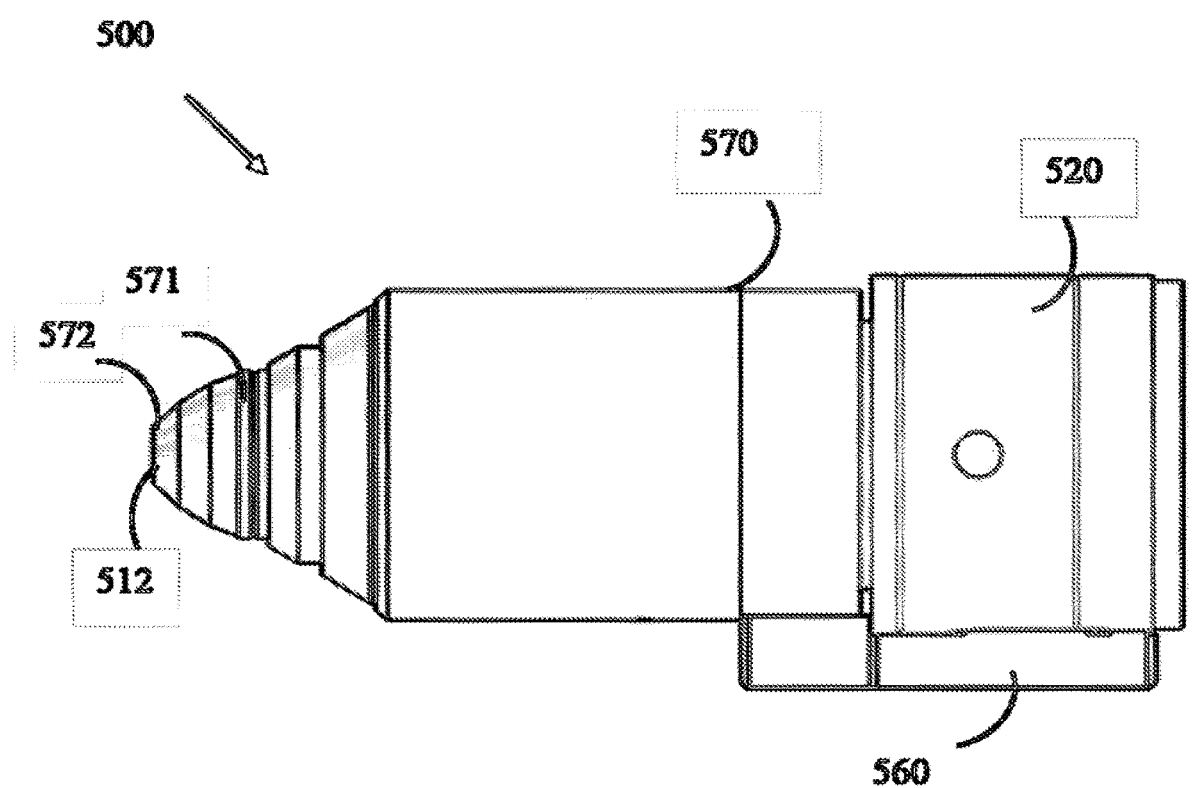
FIG. 6 shows an illustrative example of a hand piece that integrates the multiple illumination projectors, the imaging optics, a consumer image recording devices and the contact lens of the wide field fundus camera.

FIG. 6 shows an illustrative example of a hand piece 500 that integrates a central housing 570 for the multiple illumination projectors, a front housing 571 for the objective lens, an image recording device 520 and a contact lens 512 of the wide field fundus camera. In this illustrated example, the image recording device 520 is a Sony QX100 and it is affixed with the central housing 570 via a mechanical coupler 560. The contact lens 512 may be mounted on a contact lens holder 572, which is attached to the front housing 571. This way the contact lens 512 may be removed with the holder 572 for easy sterilization.

In one illustrative example, the hand piece 500 may have an elongated shape, having dimensions about 60 mm in diameter and 200 mm long. In another illustrative example, for screening for ROP, the front end of the hand piece 500 is about 10 mm in diameter.

Figure 7:
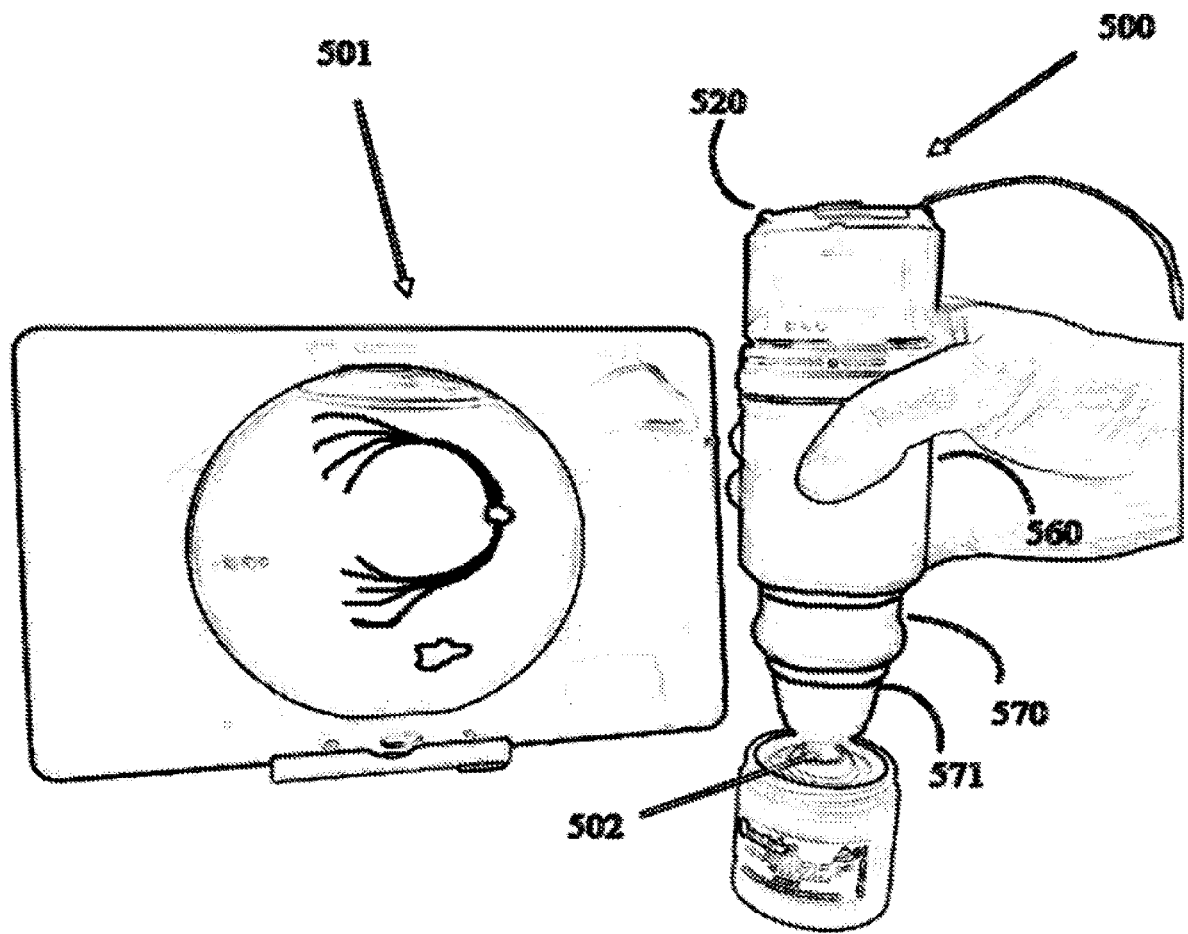
FIG. 7 shows an illustrative example hand piece with Olympus Air A01 consumer image recording device placed on a model eye and the resulting retinal image taken by the wide field fundus camera projected wirelessly over to a tablet.

FIG. 7 shows an illustrative example of a hand piece 500 that integrates a central housing 570 for the multiple illumination projectors, a front housing 571 for the objective lens, an image recording device 520 and a contact lens 512 of the wide field fundus camera. In this illustrated example, the image recording device 520 is an Olympus Air A01 (Olympus Corporation, Japan) and it is affixed with the central housing 570 via a mechanical coupler 560. In one illustrative example, images from the image recording device 520 may transmitted via Wi-Fi to a tablet display which in this illustrated example is a Samsung Galaxy Note 501.

FIG. 8 shows the tablet display for one illustrated example of the electronic controller. In this example, four independent illumination beam projectors are controlled by the electronic controller. The electronic controller serially may turn on each illumination beam projector one at a time and the image recording device 520 may capture an image with each illumination beam. 801 shows the first illumination projector beam turned on with all other beams turned off, 802 shows the second illumination projector beam turned on with all other beams turned off, 803 shows the third illumination projector beam turned on with all other beams turned off, 800 shows the fourth illumination projector beam turned on with all other beams turned off. For example, the total time to turn on and off each of the four independent beams may be less than 400 milliseconds, with 100 milliseconds for each beam. This may allow a real-time display of how the retinal image formed by each independent beam will appear to assess alignment of each independent beam projector with the eye. The pattern of serial illumination control of each independent beam projector may be controlled by the user and may be programmable by selecting one of four possible patterns 804. Each independent beam projector may be manually and independently turned on and off through a separate user control 805. Power levels for each independent illumination projection beam may be controlled by the user both for real-time live examination and flash photography level when the final photo is captured by the image recording device 806.

Figure 9:
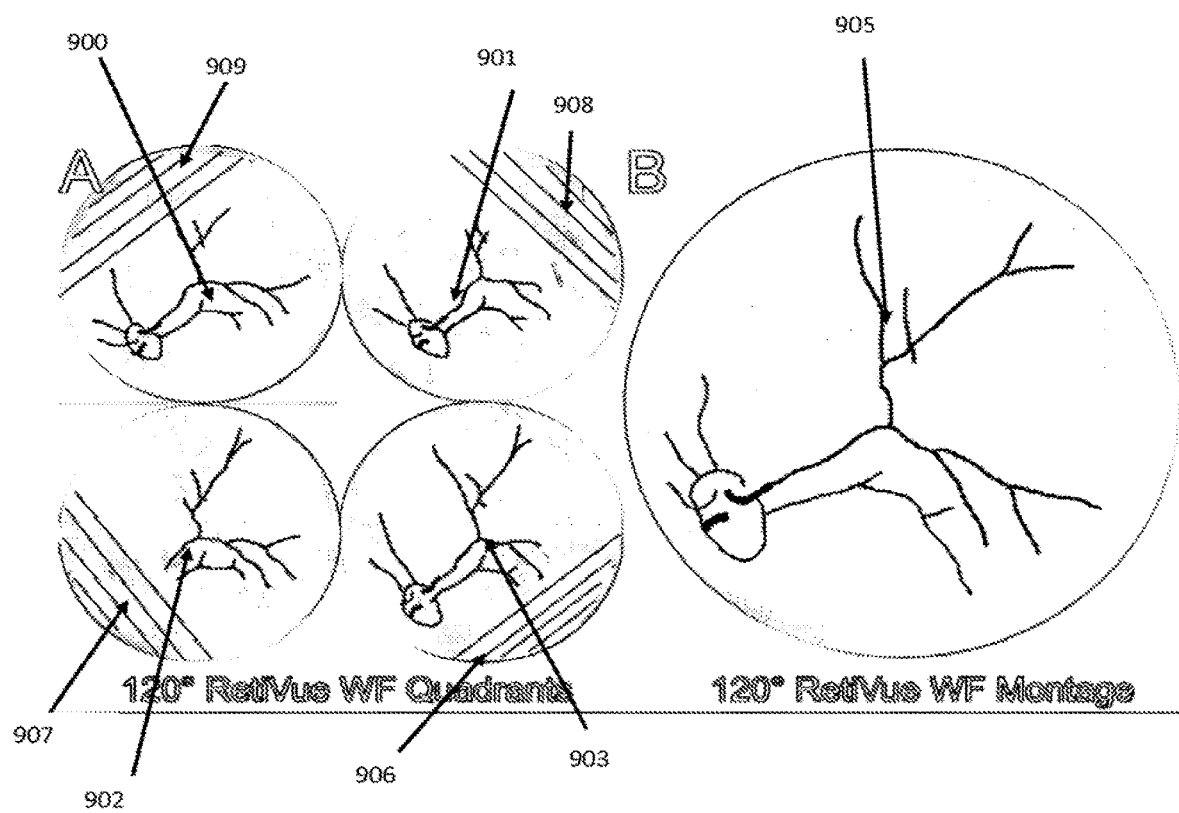
FIG. 9 shows an illustrative example of the separate retinal images formed by each of four independent projector beams. An image processing method may be used to eliminate the lens reflection haze from each projector beam, and stich together the clear aspect of the retinal image to form a final seamless montage that is adjusted to achieve even exposure across the final montaged image.

FIG. 9 shows one possible illustrated example for a method of image stitching of the plurality of images taken by independent illumination projector beams. In this example, four retinal images are taken, each having one of four independent beam projectors turned on. 901 shows the first illumination projector beam turned on with all other beams turned off, 902 shows the second illumination projector beam turned on with all other beams turned off, 903 shows the third illumination projector beam turned on with all other beams turned off, 900 shows the fourth illumination projector beam turned on with all other beams turned off. Each independent beam projector may create a specular white reflection and haze 906, 907, 908, 909, from the human lens of the eye 4 and the objective lens 10, but also illuminates a quadrant of the retina without lens haze 900, 901, 902, 903. The image processing method may remove the area in each illumination projector beam image where there is lens haze from the human lens 906, 907, 908, 909, and join together the portion of each illumination projector beam image without lens haze 900, 901, 902, 903.

Blending may be performed on the stitched pieces to seamlessly blend differences in exposure level of each illumination projector beam image. The final montage 905 may eliminate the lens haze 906, 907, 908, 909 from the montaged image. The image processing method may include a processor circuit coupled to a memory circuit, the memory circuit including instructions that cause the processor circuit to receive imaging information corresponding to the plurality of retinal images and to provide a composite image including stitching together the plurality of retinal images into a single montage image. It may further include a processor circuit coupled to a memory circuit, the memory circuit including instructions that cause the processor circuit to receive imaging information corresponding to the plurality of retinal images and remove artificial reflection spots and lens haze from each of said plurality of retinal images.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein. In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A wide field fundus camera for imaging a retina of a subject eye, comprising:

an aspherical lens having a symmetric viewing axis and disposed to form a wide field of view retinal image of the retina;

a focusing lens positioned along said viewing axis to reimage said retinal image;

an image recording device disposed to capture said reimaged retinal image;

a plurality of illumination beam projectors positioned around said viewing axis and each configured to project an illumination beam at a corresponding illumination beam angle relative to the viewing axis and toward said aspherical lens to thereby illuminate a corresponding one of a plurality of different portions of said retina within said wide field of view;

a secondary beam projector configured to project a secondary beam at a secondary beam angle relative to the viewing axis, and onto the retina to facilitate alignment and focus of the retina;

a cross polarization system incorporated between said subject eye and said image recording device, to reject specular reflections of said illumination beams; and an electronic controller configured to sequentially power said plurality of illumination beam projectors in a programmable manner and thereby facilitate capture of images of the plurality of retinal portions.

2. The wide field fundus camera of claim 1, further comprising:

a processor circuit programmed to provide a composite image by stitching together said images of the plurality of retinal portions into a single montage wide field image.

3. The wide field fundus camera of claim 1, further comprising:

a processor circuit programmed to remove artificial reflection spots and lens haze from each of said images of the plurality of retinal portions.

4. The wide field fundus camera of claim 1, wherein said aspherical lens has a field of view of 120 degrees or greater of said retina.

5. The wide field fundus camera of claim 1, wherein said focusing lens comprises an achromatic lens.

6. The wide field fundus camera of claim 1, wherein said illumination beams are each a slit beam.

7. The wide field fundus camera of claim 1, wherein said narrow secondary beam is a slit beam.

8. The wide field fundus camera of claim 1, wherein said secondary beam is a slit beam.

9. The wide field fundus camera of claim 1, wherein said secondary beam is in the infrared light spectrum.

10. The wide field fundus camera of claim 1, further comprising: a contact lens element positioned in front of said aspherical lens to contact the subject eye.

11. The wide field fundus camera of claim 1, further comprising:

a contact lens element positioned in front of said aspherical lens to contact the subject eye, said contact lens element having no optical power.

12. The wide field fundus camera of claim 1, wherein said image recording device is capable of auto focus and auto exposure.

13. A method for producing retinal image of a retina of a subject eye, the retinal image having a wide field of view, the method comprising the steps of:

providing an objective lens having a symmetric viewing axis, and configured and arranged to produce the wide field of view;

providing an image recording device disposed to capture said retinal image;

providing a plurality of illumination beam projectors positioned around said viewing axis;

projecting from each of the plurality of illumination beam projectors an illumination beam at a corresponding angle with respect to said viewing axis, wherein each illumination beam is configured to illuminate a different portion of said wide field of view;

providing a cross polarization condition incorporated between said subject eye and said image recording device to reject specular reflections of said illumination beams;

powering said plurality of illumination beam projectors in a sequential manner;

capturing a plurality of retinal images synchronized with said illumination beam projectors, wherein said plurality of retinal images are captured with the plurality of illumination beam projectors and the image recording device remaining stationary with respect to said subject eye; and producing a composite image by stitching together said plurality of retinal images into a single montage image.

14. The method of claim 13, further comprising the steps of:

removing artificial reflection spots from each of said plurality of retinal images.

15. The method of claim 13, wherein said objective lens includes an aspherical lens having a field of view of 120 degrees or wider of said retina.

16. The method of claim 13, wherein said illumination beams are slit beams.

17. The method of claim 13, further comprising the steps of:

providing a contact lens element positioned in front of said aspherical lens to contact the subject eye.

18. The method of claim 13, further comprising the steps of: providing a contact lens element positioned in front of said aspherical lens to contact the subject eye, said contact lens element having no optical power.

19. The method of claim 13, wherein said image recording device is capable of auto focus and auto exposure.

20. The method of claim 13, wherein said illumination beams are in the infrared light spectrum.

* * * * *